(12) United States Patent
Ohta et al.

(10) Patent No.: US 7,953,207 B2
(45) Date of Patent: May 31, 2011

(54) RADIATION CONVERSION PANEL AND METHOD OF CAPTURING RADIATION IMAGE THEREWITH

(75) Inventors: Yasunori Ohta, Yokohama (JP); Sadato Akahori, Odawara (JP); Kazuharu Ueta, Tokyo (JP); Atsushi Fukuda, Koganei (JP)

(73) Assignee: Fujifilm Corporation, Tokyo (JP)

( * ) Notice: Subject to any disclaimer, the term of this patent is extended or adjusted under 35 U.S.C. 154(b) by 308 days.

(21) Appl. No.: 12/239,419

(22) Filed: Sep. 26, 2008

(65) Prior Publication Data

US 2009/0086913 A1    Apr. 2, 2009

(30) Foreign Application Priority Data

Sep. 27, 2007    (JP) ................. 2007-252086

(51) Int. Cl.
*H05G 1/64* (2006.01)

(52) U.S. Cl. ............... 378/98.9; 378/98.11; 378/98.12; 250/370.09

(58) Field of Classification Search .............. 378/98.9, 378/98.11
See application file for complete search history.

(56) References Cited

U.S. PATENT DOCUMENTS

| 6,643,536 B2 | 11/2003 | Nicolas et al. |
| 6,931,098 B2 | 8/2005 | Kump et al. |
| 2005/0084073 A1* | 4/2005 | Seppi et al. ............... 378/156 |
| 2005/0212935 A1 | 9/2005 | Watanabe et al. |

FOREIGN PATENT DOCUMENTS

| JP | 2002-325756 A | 11/2002 |
| JP | 2003-284710 A | 10/2003 |
| JP | 3494683 B2 | 11/2003 |
| JP | 2005-283262 A | 10/2005 |

* cited by examiner

*Primary Examiner* — Hoon Song
*Assistant Examiner* — Mona M Sanei
(74) *Attorney, Agent, or Firm* — Sughrue Mion, PLLC

(57) ABSTRACT

A radiation conversion panel includes a first pixel group from which electric charges are read after a first energy-level image capturing cycle and after a second energy-level image capturing cycle, and a second pixel group from which electric charges are read after the second energy-level image capturing cycle, wherein pixels of the first pixel group and pixels of the second pixel group are arranged alternately.

4 Claims, 12 Drawing Sheets

RADIATION CONVERSION PANEL AND METHOD OF CAPTURING RADIATION IMAGE THEREWITH

BACKGROUND OF THE INVENTION

1. Field of the Invention

The present invention relates to a radiation conversion panel having a matrix of pixels for generating electric charges depending on a radiation that has passed through a subject, and a method of capturing a radiation image according to dual-energy radiography using such a radiation conversion panel.

2. Description of the Related Art

In the medical field, there have widely been used radiation image capturing apparatus which apply a radiation to a subject and guide the radiation that has passed through the subject to a radiation conversion panel, which captures a radiation image from the radiation. Known forms of the radiation conversion panel include a conventional radiation film for recording a radiation image by way of exposure, and a stimulable phosphor panel for storing a radiation energy representing a radiation image in a phosphor and reproducing the radiation image as stimulated light by applying stimulating light to the phosphor. The radiation film with the recorded radiation image is supplied to a developing device to develop the radiation image, or the stimulable phosphor panel is supplied to a reading device to read the radiation image as a visible image.

In the operating room or the like, it is necessary to read a recorded radiation image immediately from a radiation conversion panel after the radiation image is captured for the purpose of quickly and appropriately treating the patient. As a radiation conversion panel which meets such a requirement, there has been developed a radiation detector having a solid-state detector for converting a radiation directly into an electric charge or converting a radiation into visible light with a scintillator and then converting the visible light into an electric charge to read a detected radiation image.

Japanese Laid-Open Patent Publication No. 2005-283262 discloses a radiation detector 200 as shown in FIGS. 10 through 12 of the accompanying drawings. The radiation detector 200 comprises a sensitive semiconductor film (hereinafter also referred to as "photoelectric conversion layer") 201 for generating electric charges depending on the radiation that has passed through a subject, an active matrix substrate 202 for reading the electric charges generated by the sensitive semiconductor film 201, and a common electrode 203 for applying a bias voltage. The sensitive semiconductor film 201 may comprise a semiconductor film made of amorphous selenium (amorphous Se), CdZnTe, CdTe, $HgI_2$, $PbI_2$, or the like.

As shown in FIGS. 10 and 11, the active matrix substrate 202 has a two-dimensional matrix of individual electrodes 205 (see FIG. 10) on its surface and a charge storing and reading circuit 206 (see FIGS. 10 and 11) for storing and reading electric charges collected by the individual electrodes 205.

As shown in FIG. 11, the sensitive semiconductor film 201 and the common electrode 203 are stacked on one surfaces of the individual electrodes 205. The charge storing and reading circuit 206 comprises capacitors 206A, TFTs (Thin-Film Transistors) 206B as switching elements, and electric interconnects 206a, 206b. Each of the individual electrodes 205 is associated with one capacitor 206A and one TFT 206B.

The radiation detector 200 functions as a two-dimensional image detector which comprises a two-dimensional matrix of pixels (also referred to as "radiation detecting pixels", "radiation detecting units", or "radiation detecting elements") 220, represented by an equivalent circuit shown in FIG. 12, for detecting a two-dimensional radiation image that is projected onto the sensitive semiconductor film 201 by the radiation X that has passed through a subject.

The radiation detector 200 also has a gate drive circuit 207 (see FIGS. 10 and 12) for controlling the charge storing and reading circuit 206 and a digital image signal generator 208 (see FIG. 10) for amplifying electric charges (detected charges) read by the charge storing and reading circuit 206, into a digital image signal.

The digital image signal generator 208 comprises a plurality of integrating amplifiers 211, a multiplexer 212, and an A/D converter 213.

A process of detecting electric charges with the pixels 220 will be described below. As shown in FIG. 12, a bias voltage in the range from several kV to several tens kV output from a bias supply source 222 is supplied via a bias voltage supply lead and applied from the common electrode 203 to the sensitive semiconductor film 201. The sensitive semiconductor film 201 generates electric charges depending on the radiation X that has passed through the subject. The generated electric charges are then collected by the individual electrodes 205. Specifically, the generated electric charges move to the individual electrodes 205, inducing electric charges in the individual electrodes 205. The electric charges collected by the individual electrodes 205 are then read as electric charges i from the respective individual electrodes 205 by the charge storing and reading circuit 206.

Specifically, the gate drive circuit 207 successively applies reading signals to the gates of the TFTs 206B via the electric interconnects 206a. At the same time, the multiplexer 212 successively switches to the electric interconnects 206b that are connected to the sources of the TFTs 206B to which the reading signals are applied, supplying the electric charges stored in the capacitors 206A as electric charges (current signals) i from the TFTs 206B via the electric interconnects 206b to the integrating amplifiers 211. The current signals i are amplified by the integrating amplifiers 211, and sent as radiation detection signals of the respective individual electrodes 205 from the multiplexer 212 to the A/D converter 213, which converts the radiation detection signals into a digital image signal.

Japanese Laid-Open Patent Publication No. 2002-325756 discloses a dual-energy subtraction process for applying radiations having different energy levels at an interval of about 0.2 second to a subject which has certain different structures (e.g., a soft tissue and a bone) having respective inherent X-energy absorption characteristics, obtaining two digital image signals from a flat radiation conversion panel as an X-ray detector which is exposed to the radiations that have passed through the subject, weighting the two digital image signals with respective weighting coefficients, and subtracting one of the weighted digital image signals from the other to extract an image of one of the different structures, i.e., a soft tissue image or a bone image.

Japanese Laid-Open Patent Publication No. 2003-284710 discloses a dual-energy subtraction process for applying a radiation having a low energy level to a subject which has certain different structures (e.g., a soft tissue and a bone), reading image data from only 1024×1024 pixels of all the 2048×2048 pixels of an X-ray detector which is exposed to the radiation that has passed through the subject, then applying a radiation having a high energy level to the subject, reading image data from all the 2048×2048 pixels, and using the read two image data to produce an image representing only the soft tissue and an image representing only the bone.

According to the dual-energy subtraction process (also referred to as "two-shot energy subtraction process") disclosed in Japanese Laid-Open Patent Publication No. 2002-325756, after the first energy level is applied to the X-ray detector, the first energy-level image is read from the X-ray detector over a reading time (which is described as 130 milliseconds), and thereafter the second energy level is applied to the X-ray detector. Consequently, a relatively large motion artifact is adversely produced due to the motion of the heart of the subject between the time when the first energy-level image is captured and the time when the second energy-level image is captured.

According to the dual-energy subtraction process disclosed in Japanese Laid-Open Patent Publication No. 2003-284710, when the low-energy-level image of the subject is read in the first image capturing cycle, a 2×2 binning process is performed to read an one-pixel image from two pixels in a row and two pixels in a column, so as to shorten a radiation image acquisition time up to the second image capturing cycle for thereby preventing a motion artifact from being generated. However, the image resolution of the low-energy-level image is lowered, and there is nothing disclosed in the publication about a specific circuit arrangement for performing the 2×2 binning process.

SUMMARY OF THE INVENTION

It is an object of the present invention to provide a radiation conversion panel for capturing image data in a first energy-level image capturing cycle and a second energy-level image capturing cycle that are spaced at a reduced interval from each other, the radiation conversion panel having a specific pixel arrangement for reducing the interval between the first energy-level image capturing cycle and the second energy-level image capturing cycle and being capable of performing an energy subtraction process while maintaining a required resolution, and a method of capturing a radiation image according to dual-energy radiography using such a radiation conversion panel.

Another object of the present invention is to provide a method of capturing a radiation image according to dual-energy radiography using the radiation conversion panel for acquiring an optimum low energy-level image and an optimum high energy-level image depending on the sequence of a low energy-level image capturing cycle and a high energy-level image capturing cycle.

According to the present invention, there is provided a radiation conversion panel for use in dual-energy radiography, having a matrix of pixels for generating electric charges depending on a radiation that has passed through a subject, comprising a first pixel group from which electric charges are read after a first energy-level image capturing cycle and after a second energy-level image capturing cycle, and a second pixel group from which electric charges are read after the second energy-level image capturing cycle, wherein pixels of the first pixel group and pixels of the second pixel group are arranged alternately.

According to the present invention, the radiation conversion panel includes the first pixel group from which electric charges are read after the first energy-level image capturing cycle and after the second energy-level image capturing cycle, and the second pixel group from which electric charges are read after the second energy-level image capturing cycle, and the pixels of the first pixel group and the pixels of the second pixel group are arranged alternately, and thus, a specific pixel arrangement is clear. Further, after the first energy-level image capturing cycle, electric charges may be read from only the first pixel group. Therefore, the time interval up to the second energy-level image capturing cycle can be shortened.

In this case, the pixels of the first pixel group and the pixels of the second pixel group are arranged in a checkered pattern, whereby non-uniformity of spatial resolution is reduced in the second pixel group from which electric charges are read after the second energy-level image capturing cycle.

According to the present invention, there is also provided a method of capturing a radiation image according to dual-energy radiography according to the sequence of a high energy-level image capturing cycle and a low energy-level image capturing cycle, using a radiation conversion panel having a matrix of pixels for generating electric charges depending on a radiation that has passed through a subject, the radiation conversion panel comprising a first pixel group and a second pixel group, wherein pixels of the first pixel group and pixels of the second pixel group are arranged alternately. The method comprises a step A of performing a high energy-level image capturing cycle and thereafter reading electric charges from the pixels of the first pixel group to generate high energy-level first-pixel-group data, a step B of performing a low energy-level image capturing cycle and reading electric charges from the pixels of the second pixel group to generate high energy-level second-pixel-group data, the electric charges from the pixels of the second pixel group comprising combined electric charges of the electric charges stored due to the low energy-level image capturing cycle and the electric charges remaining after the high energy-level image capturing cycle in the step A, in the pixels of the second pixel group, a step C of reading electric charges from the pixels of the first pixel group, to generate low energy-level first-pixel-group data, a step D of copying the low energy-level first-pixel-group data generated in the step C, as low energy-level second-pixel-group data of the second pixel group, and a step E of generating subtractive image data based on high energy-level all-pixel data and low energy-level all-pixel data, the high energy-level all-pixel data comprising the high energy-level first- and second-pixel-group data, and the low energy-level all-pixel data comprising the low energy-level first- and second-pixel-group data.

With the above method, in the step A, after the high energy-level image capturing cycle is performed, the electric charges are read from the pixels of the first pixel group to generate the high-energy-level first-pixel-group data. Next, in the step B, after the low energy-level image capturing cycle is performed, the electric charges in the pixels of the second pixel group, i.e., the combination of the electric charges stored due to the low energy-level image capturing cycle, and the electric charges remaining after the high energy-level image capturing cycle in the step A, are read and then, the high energy-level second-pixel-group data is generated. Accordingly, after the high-energy-level image capturing cycle, electric charges may be read from only the first pixel group, and thus, the time interval up to the low energy-level image capturing cycle can be shortened. Also, in the step C, the electric charges are read from the pixels of the first pixel group, and the low energy-level first-pixel-group data is generated. Then, in the step D, the low energy-level first-pixel-group data generated in the step C is copied as the low energy-level second-pixel-group data of the second pixel group. Then, in the step E, the energy subtraction process is performed on the high-energy-level all-pixel data consisting of the high energy-level first- and second-pixel-group data, and the low-energy-level all-pixel data consisting of the low energy-level first- and secondpixel-group data to obtain subtractive image data. Accordingly, an energy subtraction process can be performed while a desired resolution is maintained.

According to the present invention, there is further provided a method of capturing a radiation image according to dual-energy radiography according to the sequence of a low energy-level image capturing cycle and a high energy-level image capturing cycle, using a radiation conversion panel having a matrix of pixels for generating electric charges depending on a radiation that has passed through a subject, the radiation conversion panel comprising a first pixel group and a second pixel group, wherein pixels of the first pixel group and pixels of the second pixel group are arranged alternately. The method comprises a step a of performing a low energy-level image capturing cycle and thereafter reading electric charges from the pixels of the first pixel group to generate low energy-level first-pixel-group data, a step b of performing a high energy-level image capturing cycle and reading electric charges from the pixels of the first and second pixel groups to generate high energy-level all-pixel data, a step c of copying the low energy-level first-pixel-group data generated in the step a, as low energy-level second-pixel-group data of the second pixel group, and a step d of generating subtractive image data based on the high energy-level all-pixel data and low energy-level all-pixel data, the low energy-level all-pixel data comprising the low energy-level first- and second-pixel-group data.

With the above method, in the step a, after the low energy-level image capturing cycle is performed, the electric charges are read from the pixels of the first pixel group to generate the low-energy-level first-pixel-group data. Next, in the step b, after the high energy-level image capturing cycle is performed, the electric charges in the pixels of the first and second pixel groups are read, and then, the high energy-level all-pixel data is generated. Accordingly, after the low-energy-level image capturing cycle, electric charges may be read from only the first pixel group, and thus, the time interval up to the high energy-level image capturing cycle can be shortened. Also, in the step c, the low energy-level first-pixel-group data generated in the step a is copied as the low energy-level second-pixel-group data of the second pixel group. Then, in the step d, the energy subtraction process is performed on the high-energy-level all-pixel data and the low-energy-level all-pixel data consisting of the low energy-level first- and second-pixel-group data to obtain subtractive image data. Accordingly, an energy subtraction process can be performed while a desired resolution is maintained.

With the above method also, the pixels of the first pixel group and the pixels of the second pixel group are arranged in a checkered pattern, whereby non-uniformity of spatial resolution can be reduced in the second pixel group from which electric charges are read after the second energy-level image capturing cycle.

According to the present invention, the time interval between the first energy-level image capturing cycle and the second energy-level image capturing cycle can be shortened. Further, a specific pixel arrangement can be provided, in order to shorten the time interval between the image capturing cycles. At the same time, the energy subtraction process can be performed to maintain a required resolution.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 10:
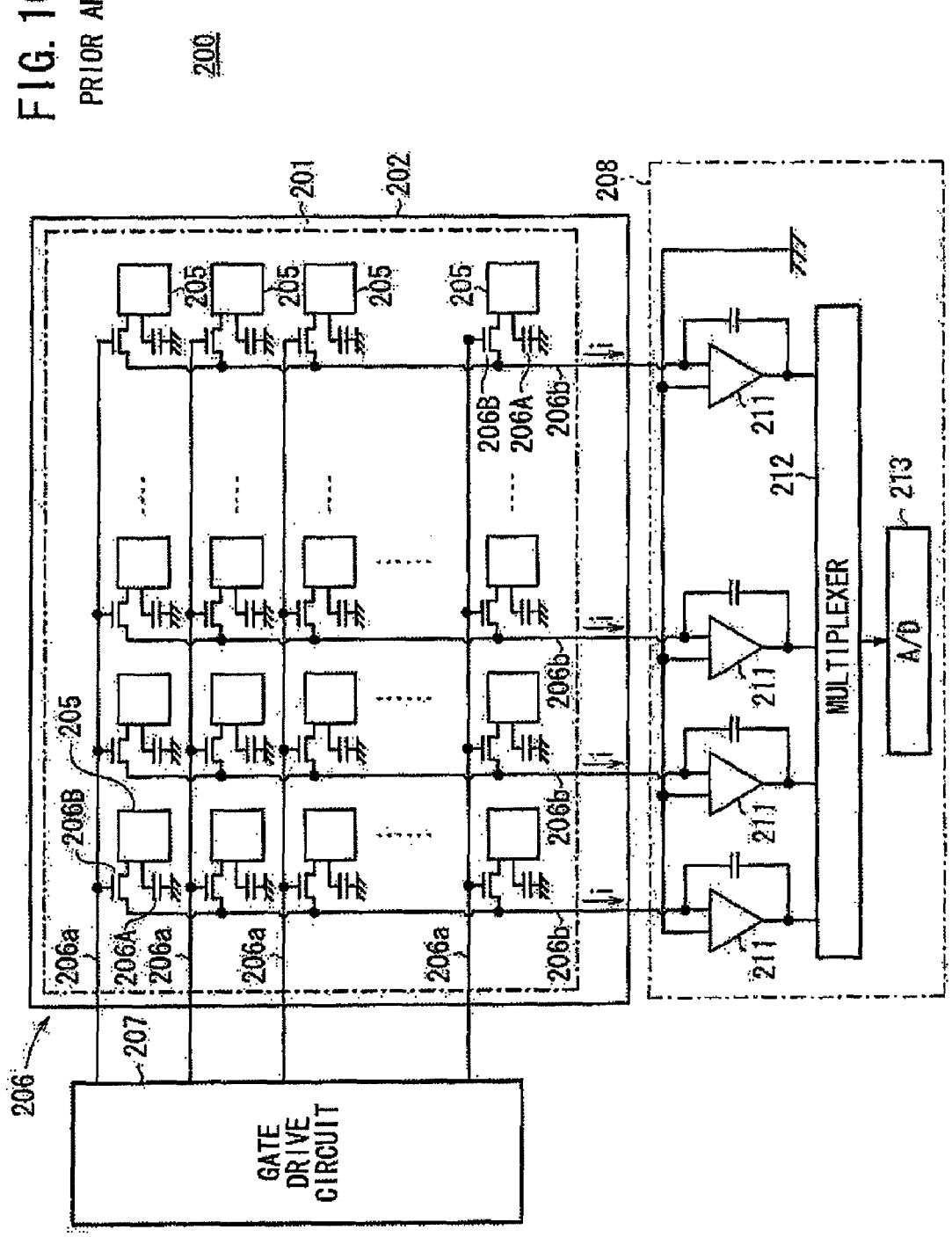
FIG. 10 is a block diagram of a circuit arrangement of a radiation detector according to the related art.
Figure 11:
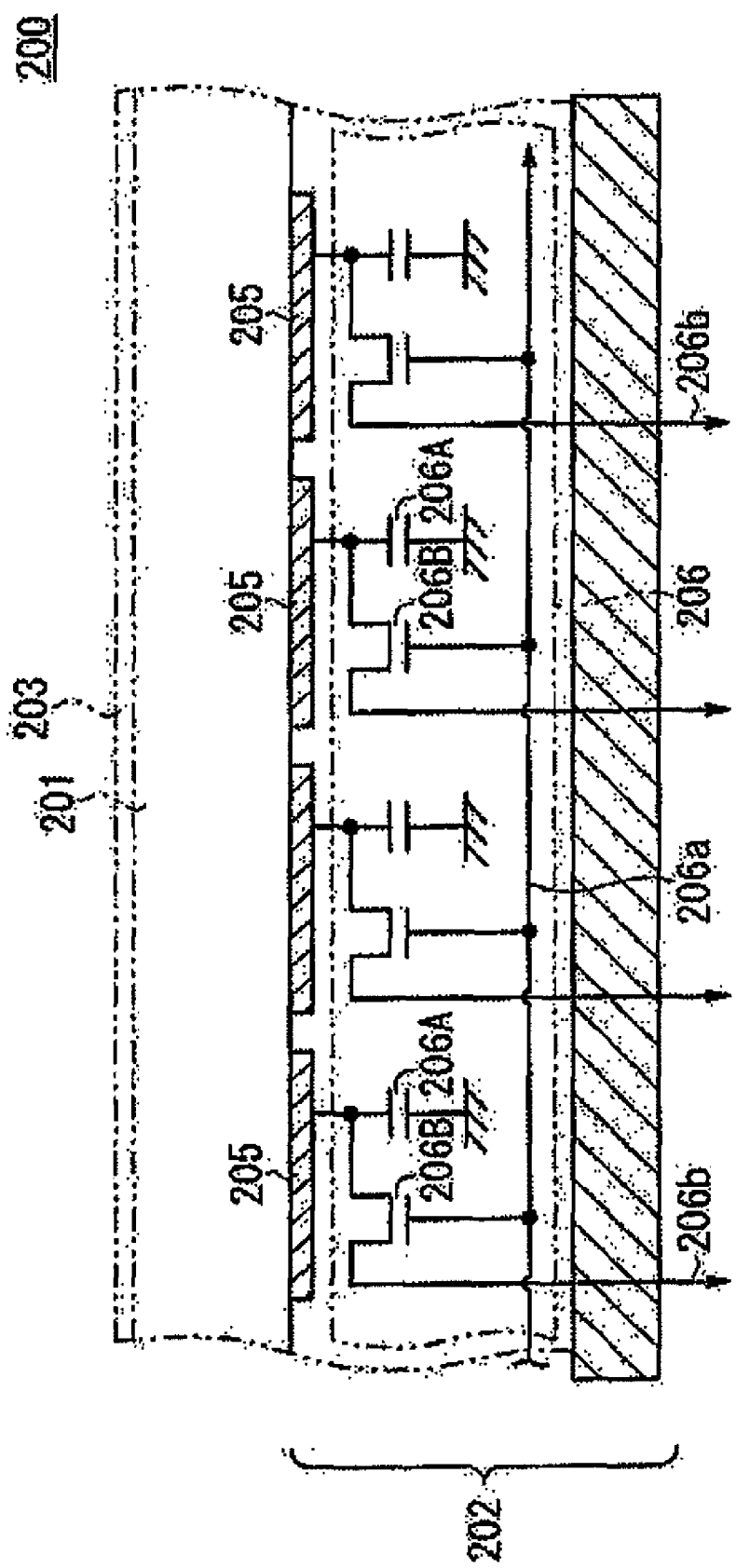
FIG. 11 is a fragmentary cross-sectional view of the radiation detector shown in FIG. 10.
Figure 12:
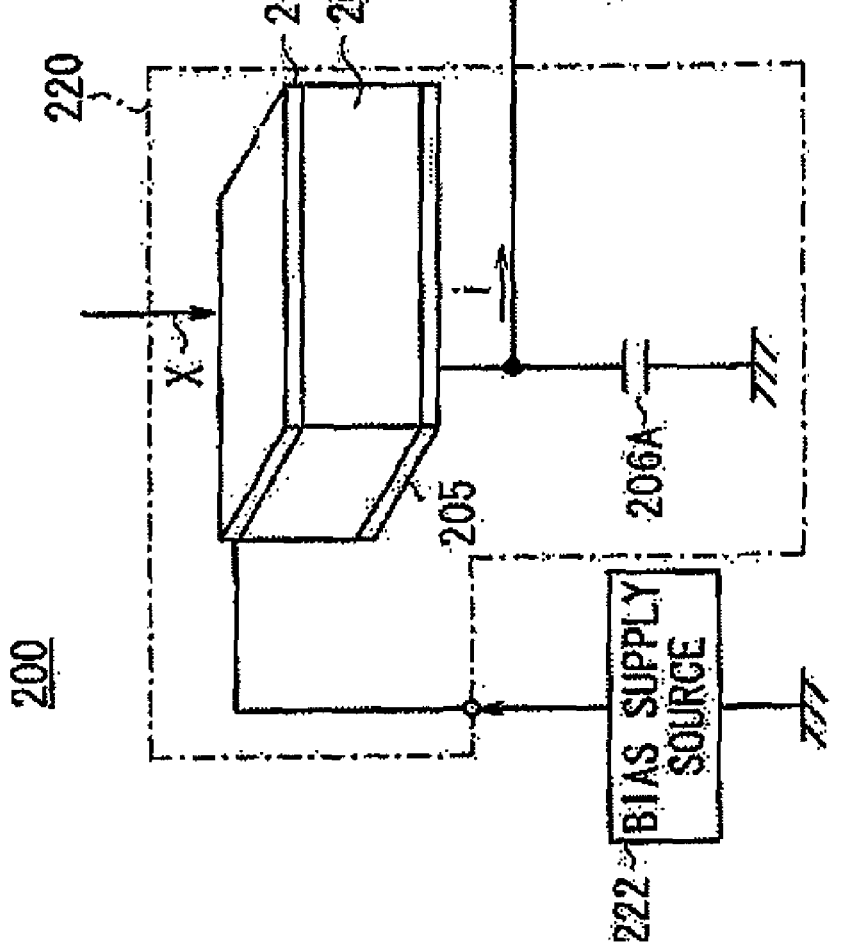
FIG. 12 is a diagram showing the manner in which the radiation detector shown in FIG. 10 operates.

Like or corresponding parts are denoted by like or corresponding reference characters throughout views. Those parts of the preferred embodiments of the present invention which are identical to those shown in FIGS. 10 through 12 are denoted by identical reference characters, and detailed explanations thereof are omitted. For the sake of brevity, FIGS. 10 through 12 will also be referred to, when necessary, in the description of the preferred embodiments of the present invention.

Figure 1:
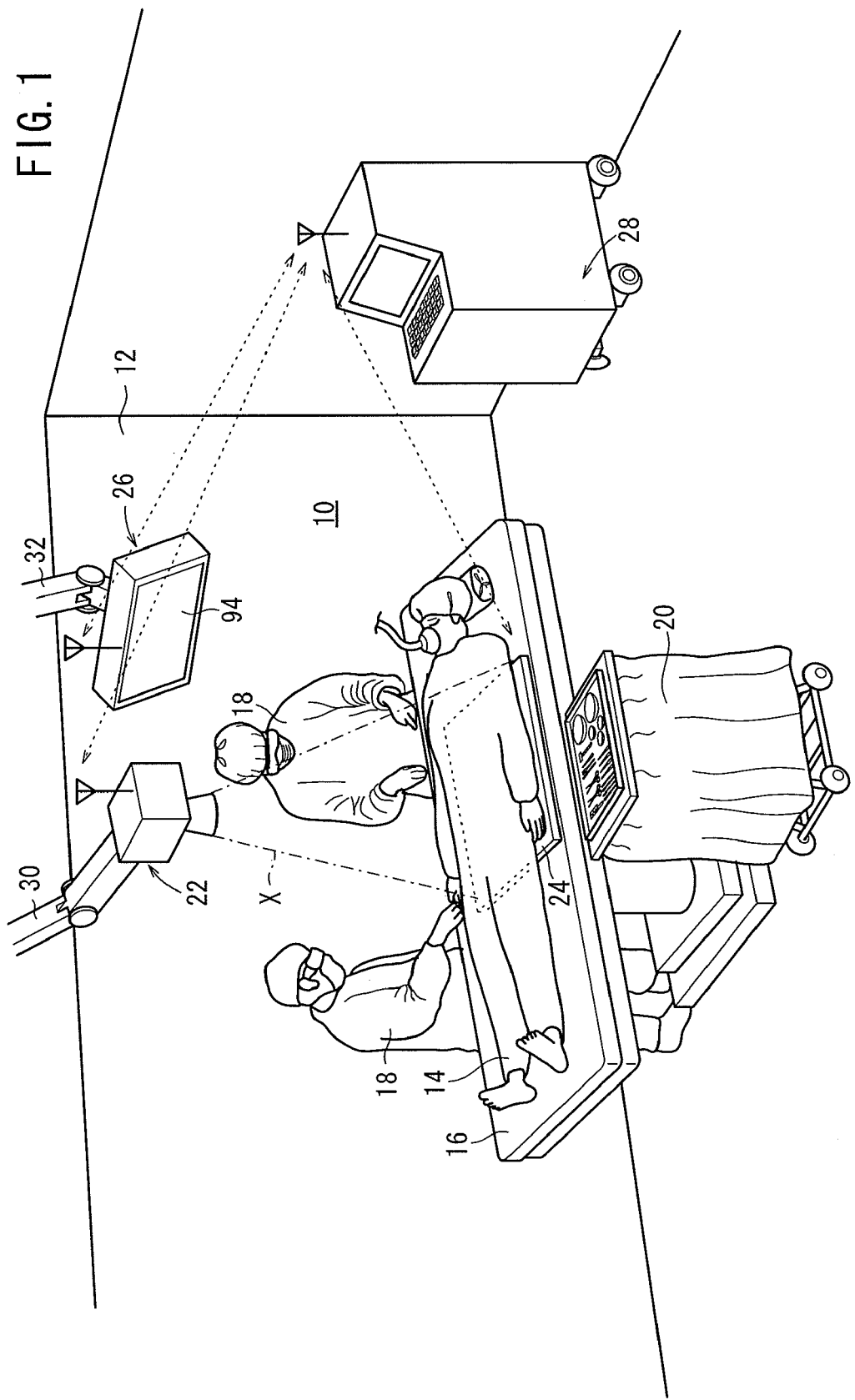
FIG. 1 is a perspective view of an operating room incorporating a radiation image capturing system according to an embodiment of the present invention.

As shown in FIG. 1, an operating room 12 incorporates a radiation image capturing system 10 according to an embodiment of the present invention. The operating room 12 has, in addition to the radiation image capturing system 10, a surgical table (bed) 16 for a patient 14 to lie thereon, and an instrument table 20 disposed on one side of the surgical table 16 for placing thereon various tools and instruments to be used by surgeons 18 for operating the patient 14. The surgical table 16 is surrounded by various apparatus required for surgical operations, including an anesthesia apparatus, an aspirator, an electrocardiograph, a blood pressure monitor, etc.

The radiation image capturing system 10 includes an image capturing apparatus 22 for irradiating the patient 14 as a subject with a radiation X at a dose according to image capturing conditions, a cassette (radiation detecting cassette) 24 housing therein a radiation detector, to be described later, for detecting the radiation X that has passed through the patient 14, a display device 26 for displaying a radiation image based on the radiation X that is detected by the radiation detector, and a console 28 for controlling the image capturing apparatus 22, the cassette 24, and the display device 26. The console 28, the image capturing apparatus 22, the cassette 24, and the display device 26 send and receive signals by way of wireless communications.

The image capturing apparatus 22 is coupled to a universal arm 30 so as to be movable to a desired position for capturing a desired area of the patient 14 and also to be retractable to a position out of the way while the surgeons 18 are performing a surgical operation on the patient 14. Similarly, the display device 26 is coupled to a universal arm 32 so as to be movable to a position where the surgeons 18 can easily confirm a captured radiation image displayed on the display device 26.

Figure 2:
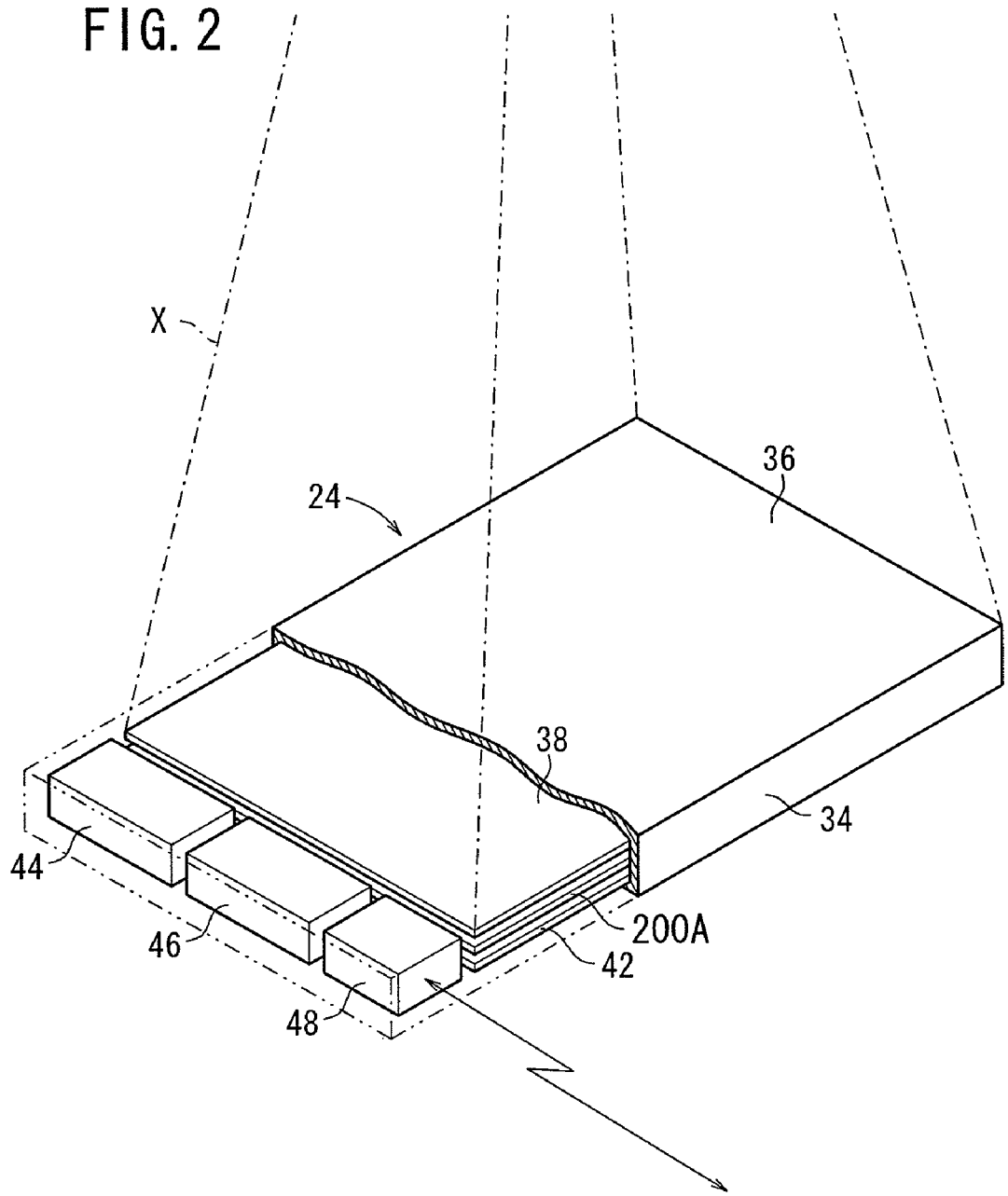
FIG. 2 is a perspective view, partly cut away, showing internal structural details of a radiation detecting cassette used in the radiation image capturing system.

FIG. 2 shows in perspective internal structural details of the cassette 24. As shown in FIG. 2, the cassette 24 has a casing 34 made of a material permeable to the radiation X. The casing 34 houses therein a grid 38 for removing scattered rays of the radiation X from the patient 14, a radiation detector (radiation conversion panel) 200A for detecting the radiation X that has passed through the patient 14, and a lead plate 42 for absorbing back scattered rays of the radiation X, which are successively arranged in the order named from a surface 36 of the casing 34 which is irradiated with the radiation X. The irradiated surface 36 of the casing 34 may be constructed as the grid 38.

The casing 34 also houses therein a battery 44 as a power supply of the cassette 24, a cassette controller 46 for energizing the radiation detector 200A with electric power supplied from the battery 44, and a cassette transceiver 48 for sending and receiving signals including the information of the radiation X detected by the radiation detector 200A, to and from the console 28. A shield plate of lead or the like should preferably be placed over the side surfaces of the cassette controller 46 and the transceiver 48 under the irradiated surface 36 of the casing 34 to protect the cassette controller 46 and the cassette transceiver 48 against damage which would otherwise be caused if irradiated with the radiation X.

Figure 3:
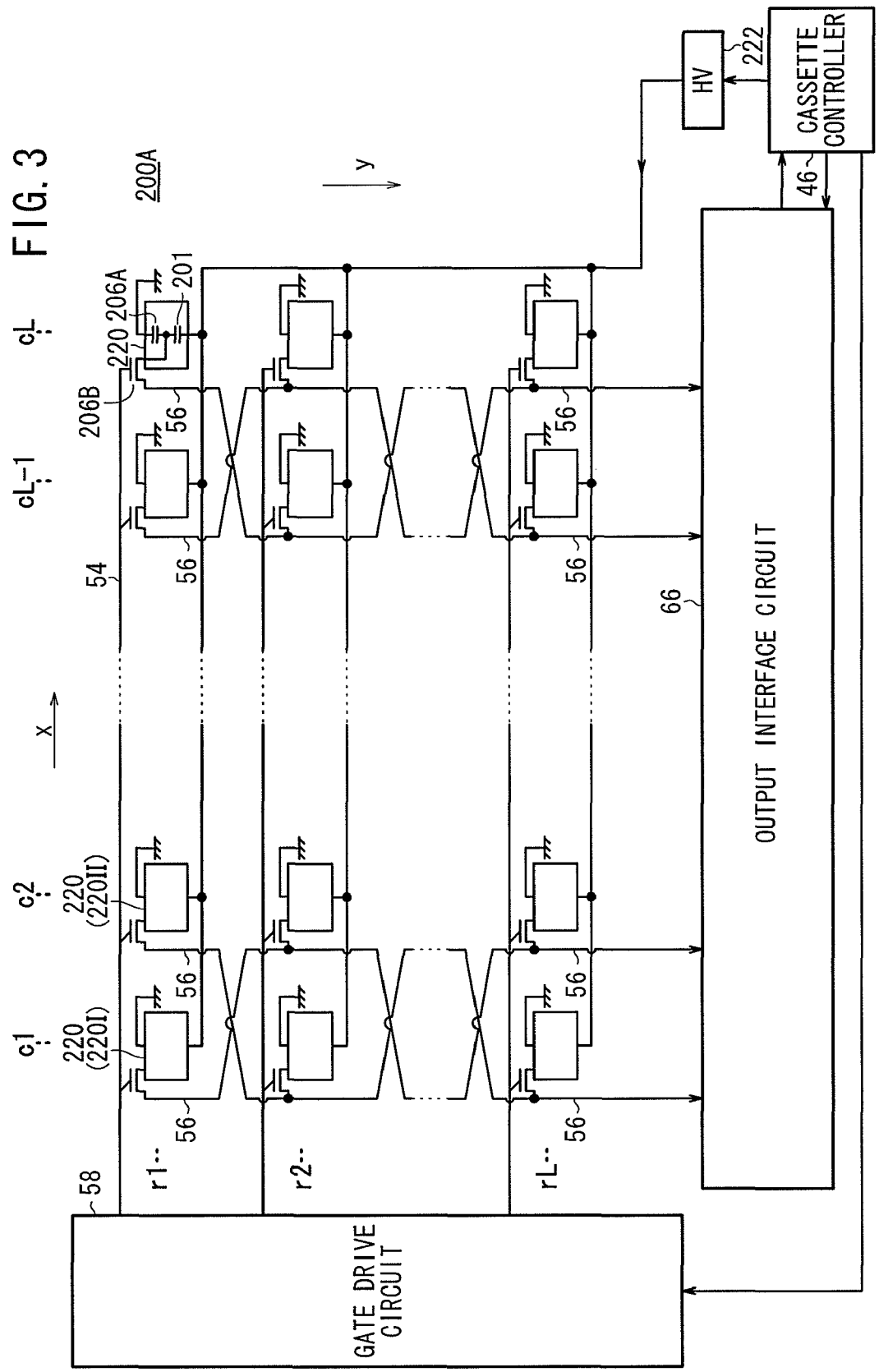
FIG. 3 is a block diagram of a circuit arrangement of a radiation detector according to the embodiment of the present invention.

FIG. 3 shows in block form a circuit arrangement of the radiation detector 200A. As shown in FIG. 3, the radiation detector 200A comprises an array of thin-film transistors (TFTs) 206B arranged in rows and columns, a photoelectric conversion layer 201 made of a material such as amorphous selenium (a-Se) for detecting a radiation X and generating electric charges when the photoelectric conversion layer 201 supplied with a high bias voltage in the range from several kV to several tens kV output from a bias supply source 222, the photoelectric conversion layer 201 being disposed on the array of TFTs 206B, and an array of capacitors 206A connected to the photoelectric conversion layer 201. When the radiation X is applied to the radiation detector 200A, the photoelectric conversion layer 201 generates electric charges, and the capacitors 206A store the generated electric charges. Then, the TFTs 206B are turned on along each row at a time to read the electric charges from the capacitors 206A as an image signal.

In FIG. 3, the photoelectric conversion layer 201 and one of the capacitors 206A are shown as a pixel 220, and the pixel 220 is connected to one of the TFTs 206B. Details of the other pixels 220 are omitted from illustration. Since amorphous selenium tends to change its structure and lose its function at high temperatures, it needs to be used in a certain temperature range. Therefore, some means for cooling the radiation detector 200A should preferably be provided in the cassette 24.

The bias supply source 222 is turned on and off by the cassette controller 46.

Figure 4:
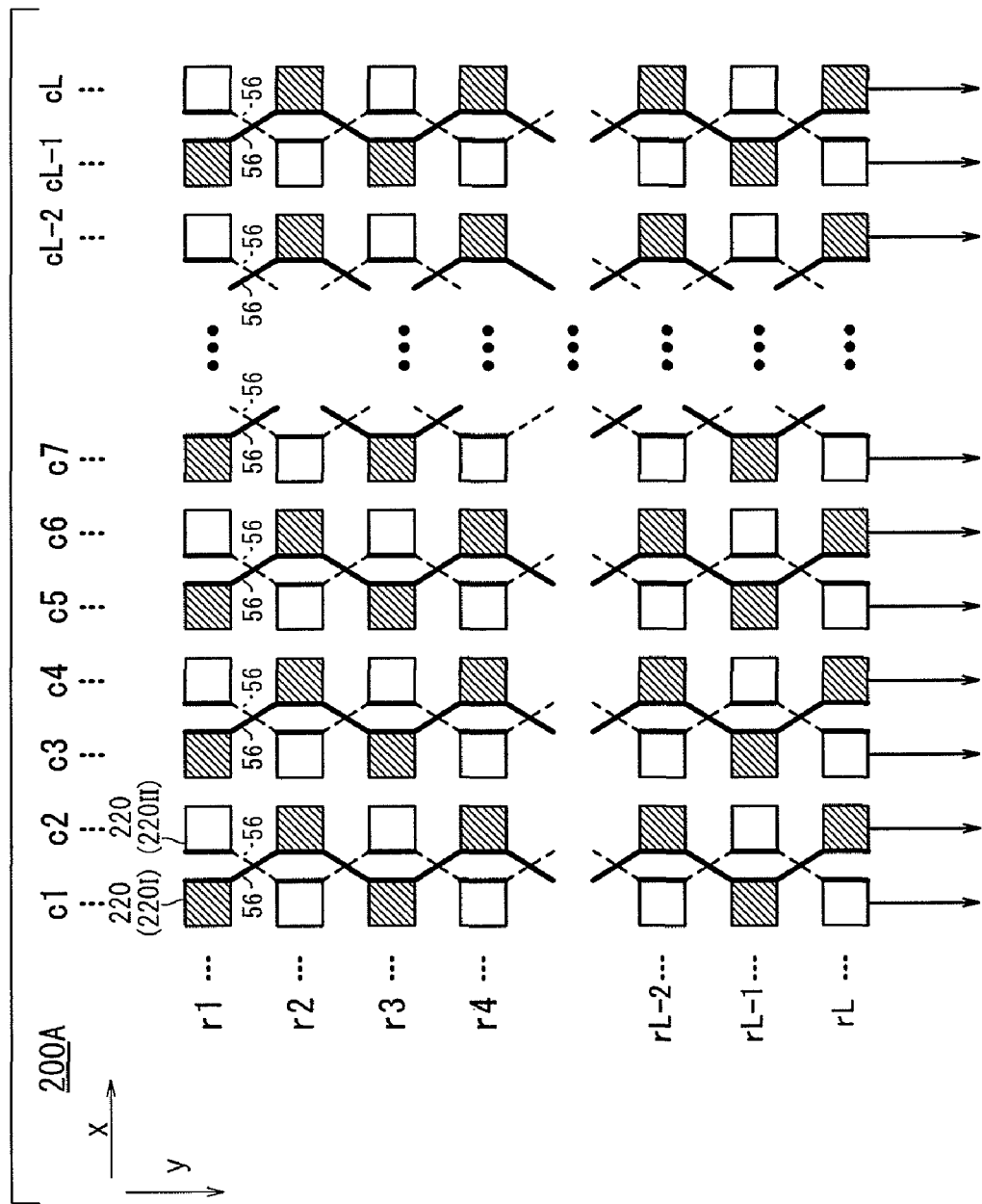
FIG. 4 is a diagram illustrative of the manner in which the radiation detector shown in FIG. 3 operates.

FIG. 4 is a diagram showing the layout of the pixels 220 of the radiation detector 200A and the manner in which electric charges are read from the pixels 220.

It is assumed for an easier understanding of the invention that the pixels 220 are arranged in a square matrix having L rows and L columns (L is an even number). Specifically, the square matrix comprises L×L pixels ranging from the pixel 220 in the first row r1 and the first column c1 to the pixel 220 in the Lth row rL and the Lth column cL. Of course, the matrix of pixels 220 is not limited to a square matrix.

As shown in FIG. 3, the TFTs 206B connected to the respective pixels 220 are connected to respective gate lines 54 extending parallel to the rows and respective signal lines 56 extending in a direction which is substantially perpendicular to the gate lines 54.

In this case, as shown in FIGS. 3 and 4, the signal lines 56 are arranged such that two signal lines 56 of a pair of two adjacent pixels 220 cross each other in each row through their respective TFTs 206B.

A pixel group consisting of pixels 220 that are represented by squares shown hatched in FIG. 4, which are ½ of all pixels, will be referred to as a first pixel group 220I. A pixel group consisting of the other pixels 220, which are represented by squares shown unhatched and also are ½ of all pixels, will be referred to as a second pixel group 220II.

As shown in FIG. 3, the gate lines 54 are connected to a gate drive circuit 58, and the signal lines 56 are connected to an output interface circuit 66.

The gate drive circuit 58 selectively turns on and off the TFTs 206B through the gate lines 54 based on a gate drive circuit control signal supplied from the cassette controller 46.

The signal lines 56 are supplied with electric charges stored in the capacitors 206A of the pixels 220 through the TFTs 206B that are turned on. The electric charges supplied to the signal lines 56 are converted into pixel data by the output interface circuit 66 based on an output interface control signal supplied from the cassette controller 46. The pixel data are supplied from the output interface circuit 66 to the cassette controller 46.

The output interface circuit 66 comprises integrating circuits with a resetting function, sample and hold circuits, A/D converters, and the like which are connected in series to the signal lines 56, respectively.

Figure 5:
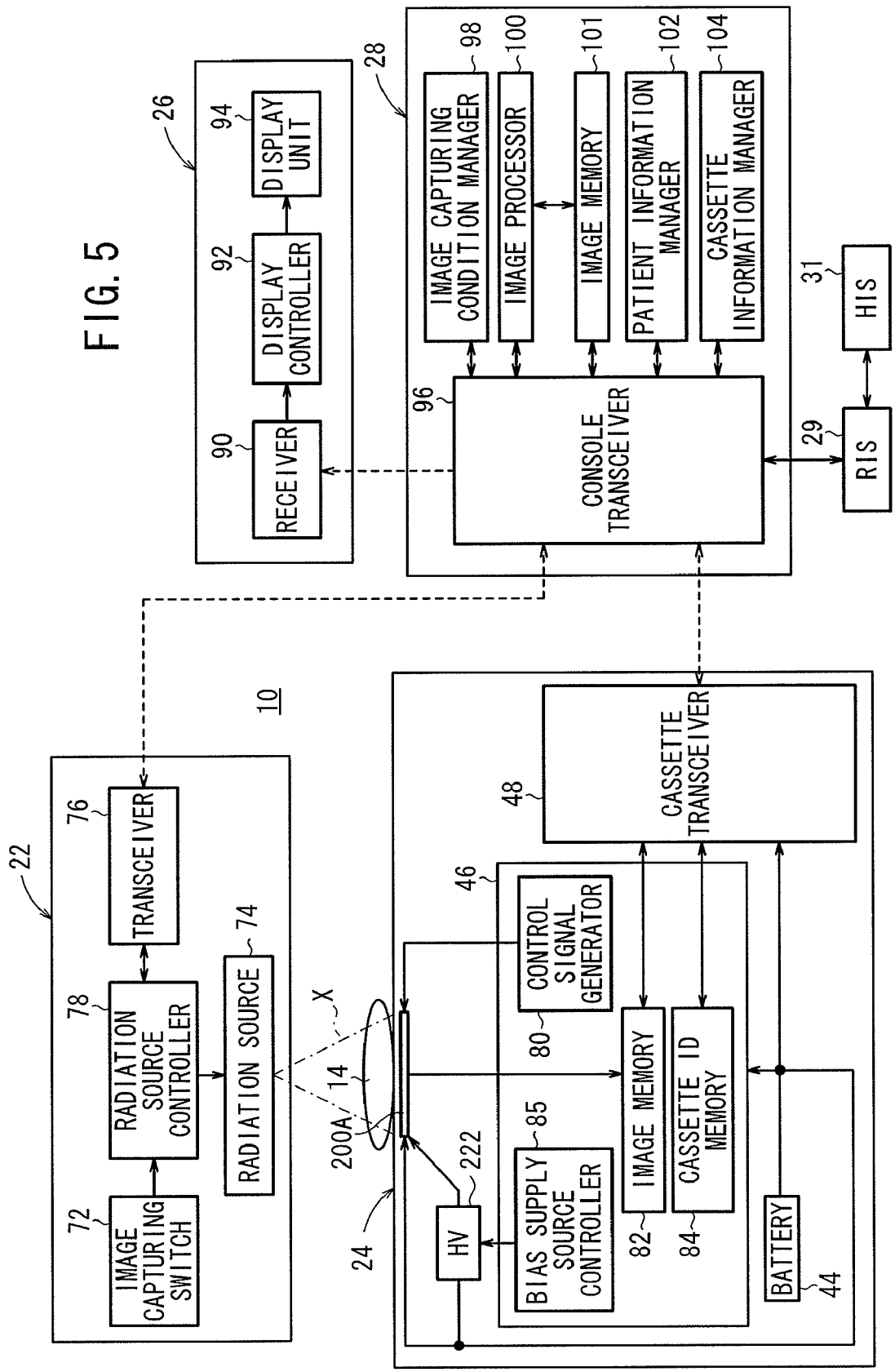
FIG. 5 is a block diagram of the radiation image capturing system.

FIG. 5 shows in block form the radiation image capturing system 10 which comprises the image capturing apparatus 22, the cassette 24, the display device 26, and the console 28. The console 28 is connected to a radiology information system (RIS) 29 which generally manages radiation image information handled by the radiological department of the hospital and other information. The RIS 29 is connected to a hospital information system (HIS) 31 which generally manages medical information in the hospital.

The image capturing apparatus 22 comprises an image capturing switch 72, a radiation source 74 for outputting the radiation X, a transceiver 76 for receiving image capturing conditions from the console 28 by way of wireless communications and transmitting an image capturing process in-progress signal, etc. to the console 28 by way of wireless communications, and a radiation source controller 78 for controlling the radiation source 74 based on an image capturing start signal supplied from the image capturing switch 72 and image capturing conditions supplied from the transceiver 76.

The radiation source controller 78 has a function to switch the irradiation energy of the radiation X that is output from the radiation source 74 based on the image capturing conditions between a high energy level and a low energy level.

The cassette 24 houses therein the radiation detector 200A, the battery 44, the cassette controller 46, and the cassette transceiver 48.

The cassette controller 46 comprises a control signal generator 80 for supplying a gate drive control signal to the gate drive circuit 58 of the radiation detector 200A and also supplying an output interface control signal to the output interface circuit 66, an image memory 82 for storing the radiation image information detected by the radiation detector 200A, a cassette ID memory 84 for storing cassette ID information for identifying the cassette 24, and a bias supply source controller (bias supply source on/off controller) 85 for turning on and off the bias supply source 222.

The cassette transceiver 48 receives various signals representing image capturing conditions, etc. from the console 28 by way of wireless communications and transmits the cassette ID information stored in the cassette ID memory 84 and the radiation image information stored in the image memory 82 to the console 28 by way of wireless communications.

The display device 26 comprises a receiver 90 for receiving the radiation image information from the console 28, a display controller 92 for controlling the display of the received radiation image information, and a display unit 94 for displaying the radiation image information processed by the display controller 92.

The console 28 comprises a console transceiver 96 for transmitting and receiving necessary information including radiation image information to and from the image capturing apparatus 22, the cassette 24, and the display device 26 by way of wireless communications, an image capturing condition manager 98 for managing image capturing conditions required for the image capturing apparatus 22 to capture radiation images, an image processor (image processing means) 100 for processing radiation image information transmitted from the cassette 24 according to a dual-energy subtraction process, etc., an image memory 101 for storing the radiation image information before and after the process by the image processor 100, a patient information manager 102 for managing patient information of the patient 14 whose images are to be captured, and a cassette information manager 104 for managing the cassette information.

The console 28 may be located outside of the operating room 12 insofar as it can transmit and receive signals to and from the image capturing apparatus 22, the cassette 24, and the display device 26 by way of wireless communications.

The image capturing conditions refer to conditions for determining a tube voltage, a tube current, an irradiation time, etc. required to apply a radiation X at an appropriate dose to an area to be imaged of the patient 14. The image capturing conditions may include an area to be imaged of the patient 14, an image capturing method, etc., for example. The patient information refers to information for identifying the patient 14, such as the name, gender, patient ID number, etc. of the patient 14. Ordering information for instructing the radiation image capturing system 10 to capture a radiation image, including the image capturing conditions and the patient information, can be set directly on the console 28 or can be supplied from an external source to the console 28 via the RIS 29. The cassette information refers to cassette ID information for identifying the cassette 24.

The radiation image capturing system 10 according to the present embodiment is basically constructed as described above, and operation of the radiation image capturing system 10 will be described below with reference to a flowchart shown in FIG. 6.

The radiation image capturing system 10 is installed in the operating room 12 and used when a radiation image of the patient 14 is required by the surgeons 18 who are performing a surgical operation on the patient 14. Before a radiation image of the patient 14 is captured, patient information of the patient 14 to be imaged is registered beforehand in the patient information manager 102 of the console 28. If an area to be imaged of the patient 14 and an image capturing method have already been known, they are registered beforehand as image capturing conditions in the image capturing condition manager 98.

It is assumed that the radiation image capturing system 10 captures a diagnostic image of a soft part of the chest of the patient 14 based on the radiation X which is set to a high energy level. For keeping a desired resolution of the diagnostic image, the radiation image capturing system 10 carries out a high energy-level image capturing cycle (first shot) and then a low energy-level image capturing cycle (second shot) (two-shot dual-energy image capturing process).

If the radiation image capturing system 10 is to capture a diagnostic image of a soft part of the abdomen of the patient 14, then the radiation image capturing system 10 captures the diagnostic image based on the radiation X which is set to a low energy level. In this case, as described later, for keeping a desired resolution of the diagnostic image, the radiation image capturing system 10 carries out a low energy-level image capturing cycle and then a high energy-level image capturing cycle (two-shot dual-energy image capturing process).

Figure 6:
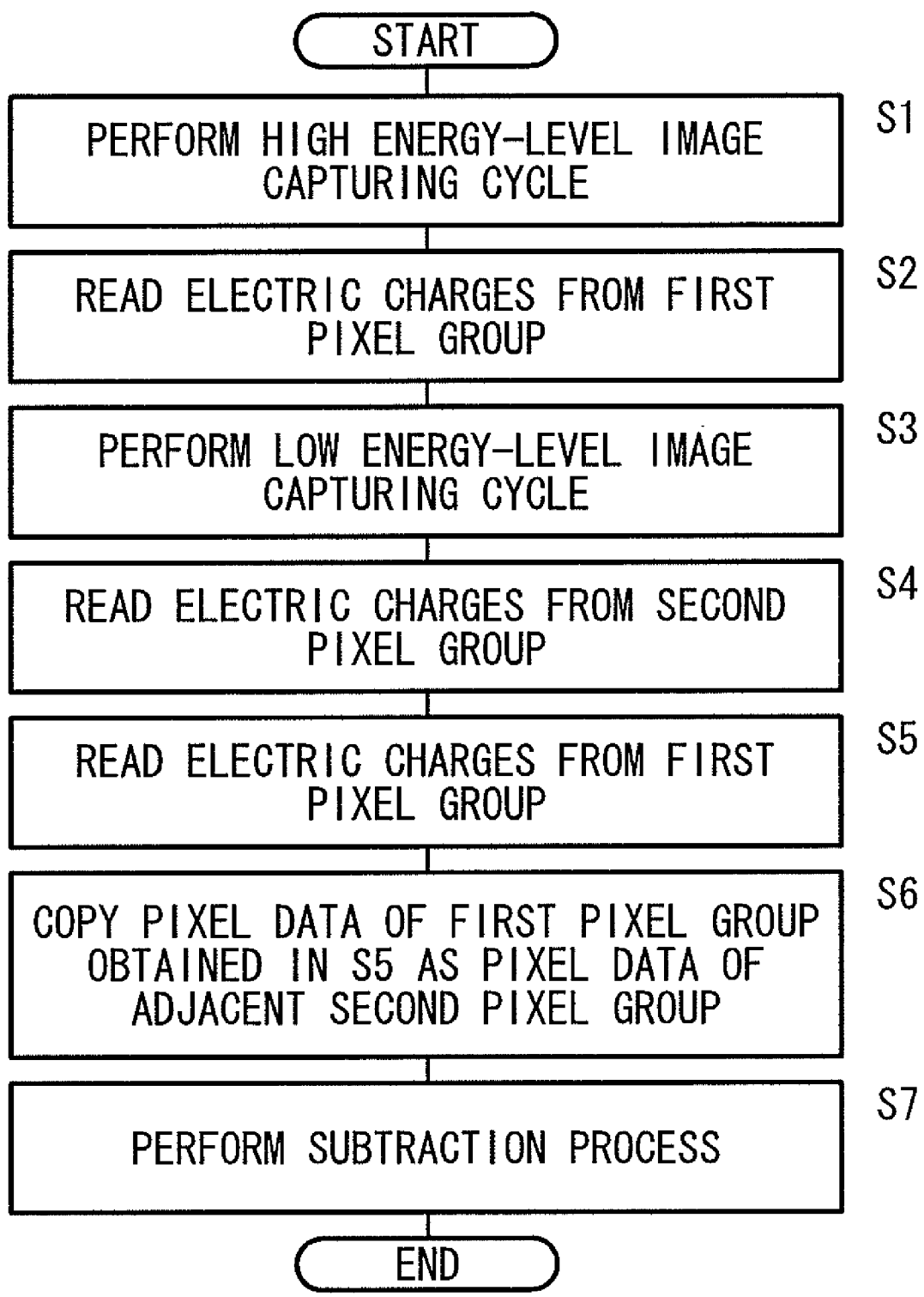
FIG. 6 is a flowchart of an operation sequence of the radiation image capturing system for acquiring a soft chest part image.

The flowchart shown in FIG. 6 is representative of the two-shot dual-energy image capturing process for capturing a soft chest part image of the patient 14.

After the above preparatory process is finished, the surgeons 18 perform a surgical operation on the patient 14.

For capturing a radiation image of the patient 14 during the surgical operation, one of the surgeons 18 or the radiological technician in charge of the surgical operation places the cassette 24 at a predetermined position between the patient 14 and the surgical table 16 with the irradiated surface 36 facing the image capturing apparatus 22.

After having moved the image capturing apparatus 22 to a position facing the cassette 24, one of the surgeons 18 or the radiological technician turns on the image capturing switch 72.

The radiation source controller 78 of the image capturing apparatus 22 acquires the image capturing conditions for an area to be imaged of the patient 14 from the image capturing condition manager 98 of the console 28 via the console transceiver 96 and the transceiver 76 by way of wireless communications. According to the acquired image capturing conditions, the radiation source controller 78 then controls the radiation source 74 to apply a high-energy-level radiation X at a given dose to the patient 14 (a high energy-level image capturing cycle, a first shot) in step S1.

The high-energy-level radiation X which has passed through the patient 14 is applied to the grid 38 of the cassette 24, which removes scattered rays of the radiation X. Then, the high-energy-level radiation X is applied to the radiation detector 200A, and converted into electric signals by the photoelectric conversion layer 201 of the pixels 220 of the radiation detector 200A. The electric signals are stored as electric charges in the capacitors 206A.

The stored electric charge information, which represents radiation image information of the patient 14 and which is stored in the capacitors 206A, are read from the capacitors 206A according to the gate drive circuit control signal supplied from the control signal generator 80 of the cassette controller 46 to the gate drive circuit 58 and the output interface control signal supplied from the control signal generator 80 to the output interface circuit 66.

In step S2, the electric charges are read as image information from the pixels 220 shown hatched in FIG. 4, which make up the first pixel group 220I and which are ½ of the entire pixels 220, and supplied as high-energy-level first-pixelgroup data Sh1 through the output interface circuit 66 to the image memory 82 where they are temporarily stored, and also through the cassette transceiver 48 and the console transceiver 96 to the image memory 101 where they are temporarily stored. At this time, the capacitors 206A of the remaining pixels 220 shown unhatched, which make up the second pixel group 220II and which are ½ of all the pixels 220, store therein electric charges according to the high-energy-level radiation X.

In step S3, the radiation source controller 78 of the image capturing apparatus 22 controls the radiation source 74 according to the acquired image capturing conditions to apply a low-energy-level radiation X at a given dose to the patient 14 (a low energy-level image capturing cycle, a second shot).

The low-energy-level radiation X which has passed through the patient 14 is applied to the grid 38 of the cassette 24, which removes scattered rays of the radiation X. Then, the low-energy-level radiation X is applied to the radiation detector 200A, and converted into electric signals by the photoelectric conversion layer 201 of the pixels 220 of the radiation detector 200A. The electric signals are stored as electric charges in the capacitors 206A.

In step S4, electric charges (i.e., combination of the remaining electric charges due to the high-energy-level radiation X in the above step S1 and the electric charges due to the low-energy-level radiation X which have been stored in the above step S3) are read, as image information, from the pixels 220, shown unhatched, of the second pixel group 220II. The read electric charges are supplied as high-energy-level second-pixel-group data Sh2 through the output interface circuit 66 to the image memory 82 where they are temporarily stored, and also through the cassette transceiver 48 and the console transceiver 96 to the image memory 101 where they are temporarily stored. When the high-energy-level second-pixel-group data Sh2 is to be stored in the image memory 101, levels of pixel values of pixel data in the data Sh2 is adjusted by the image processor 100, and then, the data Sh2 is stored, in order to offset the increase in the pixel values due to the low-energy-level radiation X.

At this time, the image memory 101 stores therein high-energy-level all-pixel data (Sh1+Sh2=SH) consisting of the high-energy-level first-pixel-group data Sh1 and the adjusted high-energy-level second-pixel-group data Sh2.

In step S5, electric charges are read from the pixels 220, shown hatched in FIG. 4, of the first pixel group 220I. The read electric charges are supplied as low-energy-level first-pixel-group data SL1 through the output interface circuit 66 to the image memory 82 where they are temporarily stored, and also through the cassette transceiver 48 and the console transceiver 96 to the image memory 101 where they are temporarily stored. At this time, there is no electric charge in the pixels 220, shown unhatched, of the second pixel group 220II, because the electric charges have already been read from the pixels 220 of the second pixel group 220II.

In step S6, in order to generate data for the nonexistent low-energy-level second pixel group 220II, the low-energy-level first-pixel-group data SL1 obtained in step S5 is copied as pixel data (low-energy-level second-pixel-group data SL2) of the second pixel group 220II for each adjacent pixel and stored at corresponding pixel data address positions in the image memory 101. Specifically, for example, pixel data of the pixel 220 in the first row r1 and the first column c1 is copied as pixel data of the adjacent pixel 220 in the first row r1 and the second column c2, and pixel data of the pixel 220 in the second row r2 and the second column c2 is copied as pixel data of the pixel 220 in the second row r2 and the first column c1. In this manner, the low-energy-level all-pixel data (SL1+SL2=SL) is stored in the image memory 101.

In step S7, the low-energy-level all-pixel data SL and the high-energy-level all-pixel data SH that are stored in the image memory 101 are frequency-processed, weighted, and then subtracted one from the other by the image processor 100, thereby producing subtractive image data. The subtractive image data represent radiation image information of a particular structure, i.e., in this case, the soft chest part from which the bones are removed. The soft chest part radiation image information is stored in the image memory 101.

The soft chest part radiation image information is stored in the image memory 101 in association with the patient information of the patient 14 registered in the patient information manager 102.

The soft chest part radiation image information stored in the image memory 101 is transmitted from the console transceiver 96 to the display device 26 where it is received by the receiver 90. In the display device 26, the display controller 92 controls the display unit 94 to display a radiation image of the soft chest part based on the soft chest part radiation image information. The radiation image of the soft chest part displayed on the display unit 94 is used for a diagnosis by the surgeons 18.

According to the present embodiment, as described above, the method of capturing a radiation image according to dual-energy radiography based on the sequence of a high energy-level image capturing cycle and a low energy-level image capturing cycle employs the radiation detector (radiation conversion panel) 200A which comprises the matrix of pixels 220 for generating electric charges depending on the radiation X that has passed through the patient 14 as a subject. In the radiation detector 200A, pixels 220 of the first pixel group 220I and pixels 220 of the second pixel group 220II are arranged alternately into a checkered pattern.

After the high energy-level image capturing cycle is performed (step S1), the electric charges are read from the pixels 220 of the first pixel group 220I (step S2) to generate the high-energy-level first-pixel-group data Sh1 (step A).

Next, after the low energy-level image capturing cycle is performed (step S3), the electric charges in the pixels 220 of the second pixel group 220II, i.e., the combination of the electric charges stored due to the low energy-level image capturing cycle in the above step S3, and the electric charges remaining after the high energy-level image capturing cycle in the step A, are read (step S4). Then, the high energy-level second-pixel-group data Sh2 is generated (step B).

Next, the electric charges are read from the pixels 220 of the first pixel group 220I (step S5), and the low energy-level first-pixel-group data SL1 is generated (step C).

Then, the generated low energy-level first-pixel-group data SL1 is copied as the low energy-level second-pixel-group data SL2 for the adjacent second pixel group 220II (step S6, step D).

Finally, the energy subtraction process is performed on the high-energy-level all-pixel data SH consisting of the high energy-level first- and second-pixel-group data, levels of which have been adjusted as necessary, and the low-energy-level all-pixel data SL consisting of the low energy-level first- and second-pixel-group data (step S7) to obtain the soft chest part radiation image information representing a desired radiation image information made of subtractive image data (step E).

After the high energy-level image capturing cycle in the step S1, only the electric charges stored in the pixels 220 of the first pixel group 220I, which are ½ of the entire pixels 220, may be read. Consequently, the time interval up to the low energy-level image capturing cycle is shortened to reduce a motion artifact. At the same time, since the high energy image as the diagnostic image of the soft part of the chest of the patient 14, from which the bone parts are removed, is based on the high-energy-level all-pixel data SH consisting of the high energy-level first- and second-pixel-group data (Sh1 +Sh2), the energy subtraction process can be performed while maintaining a desired resolution of the soft chest part radiation image.

Since the pixels 220 of the first pixel group 220I and the pixels 220 of the second pixel group 220II are arranged checkerwise, nonuniformity of the space resolution is reduced.

As described above, when a soft part of an abdominal part of the patient 14 is to be imaged, then a diagnostic image of the abdominal part is generated based on the low-energy-level radiation X. In this case, in order to maintain a desired resolution of the diagnostic image, the method of capturing a radiation image according to two-shot dual-energy radiography based on the sequence of a low energy-level image capturing cycle and a high energy-level image capturing cycle is employed.

Figure 7:
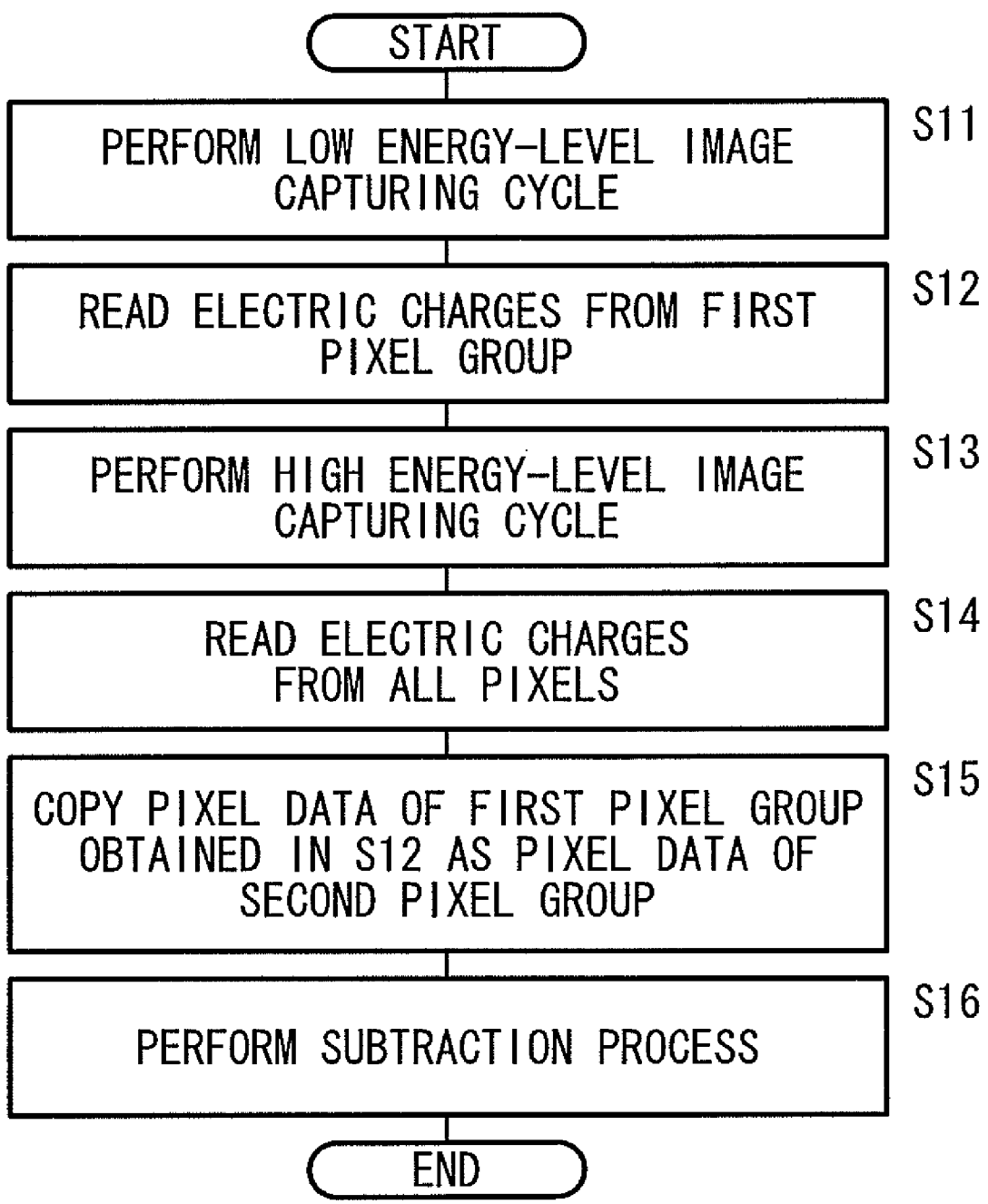
FIG. 7 is a flowchart of an operation sequence of the radiation image capturing system for acquiring a soft abdominal part image.

FIG. 7 is a flowchart which is representative of the two-shot dual-energy image capturing process for capturing a soft abdominal part image of the patient 14.

To explain it simply, in step S11 shown in FIG. 7, a low-energy-level radiation X is applied at a given dose to the patient 14 (a low energy-level image capturing cycle, a first shot).

In step S12, the electric charges stored in the pixels 220 of the first pixel group 220I, which are shown hatched in FIG. 4.

Immediately thereafter, in step S13, the radiation source controller 78 controls the radiation source 74 according to the acquired image capturing conditions to apply a high-energy-level radiation X at a given dose to the patient 14 (a high energy-level image capturing cycle, a second shot).

In step S14, the electric charges are read from all the pixels. In this case, the electric charges due to the high energy-level radiation X, which have been stored in the pixels 220 of the first pixel group 220I in the above step S13, and the combination of the electric charges due to the low-energy-level radiation X, which remains in the pixels 220 of the second pixel group 220II and the electric charges due to the high-energy-level radiation X, which have been stored in the pixels 220 of the second pixel group 220II in the above step S13, are read as image information. The read electric charges are supplied as high-energy-level all-pixel data SH through the output interface circuit 66 to the image memory 82 where they are temporarily stored, and also through the cassette transceiver 48 and the console transceiver 96 to the image memory 101 where they are temporarily stored. When the high-energy-level all-pixel data SH is stored in the image memory 101, levels of pixel values of pixel data in the second pixel group 220II is adjusted by the image processor 100, and then, the data SH is stored, in order to offset the increase in the pixel values due to the low-energy-level radiation X.

In step S15, the pixel data of the first pixel group obtained in step S12 is copied as the pixel data of the adjacent second pixel group to generate low-energy-level all-pixel data SL.

Finally, in step S16, the low-energy-level all-pixel data SL and the high-energy-level all-pixel data SH are subtracted one from the other by the image processor 100, thereby producing subtractive image data representing a soft abdominal part image. Since the soft abdominal part image is based on the low-energy-level all-pixel data SL, the resolution thereof is not lowered. In the interval between the low energy-level image capturing cycle and the high energy-level image capturing cycle, the electric charges are read from only the pixels that are ½ of all the pixels. Therefore, the time interval between the image capturing cycles is shortened to reduce a motion artifact.

Figure 8:
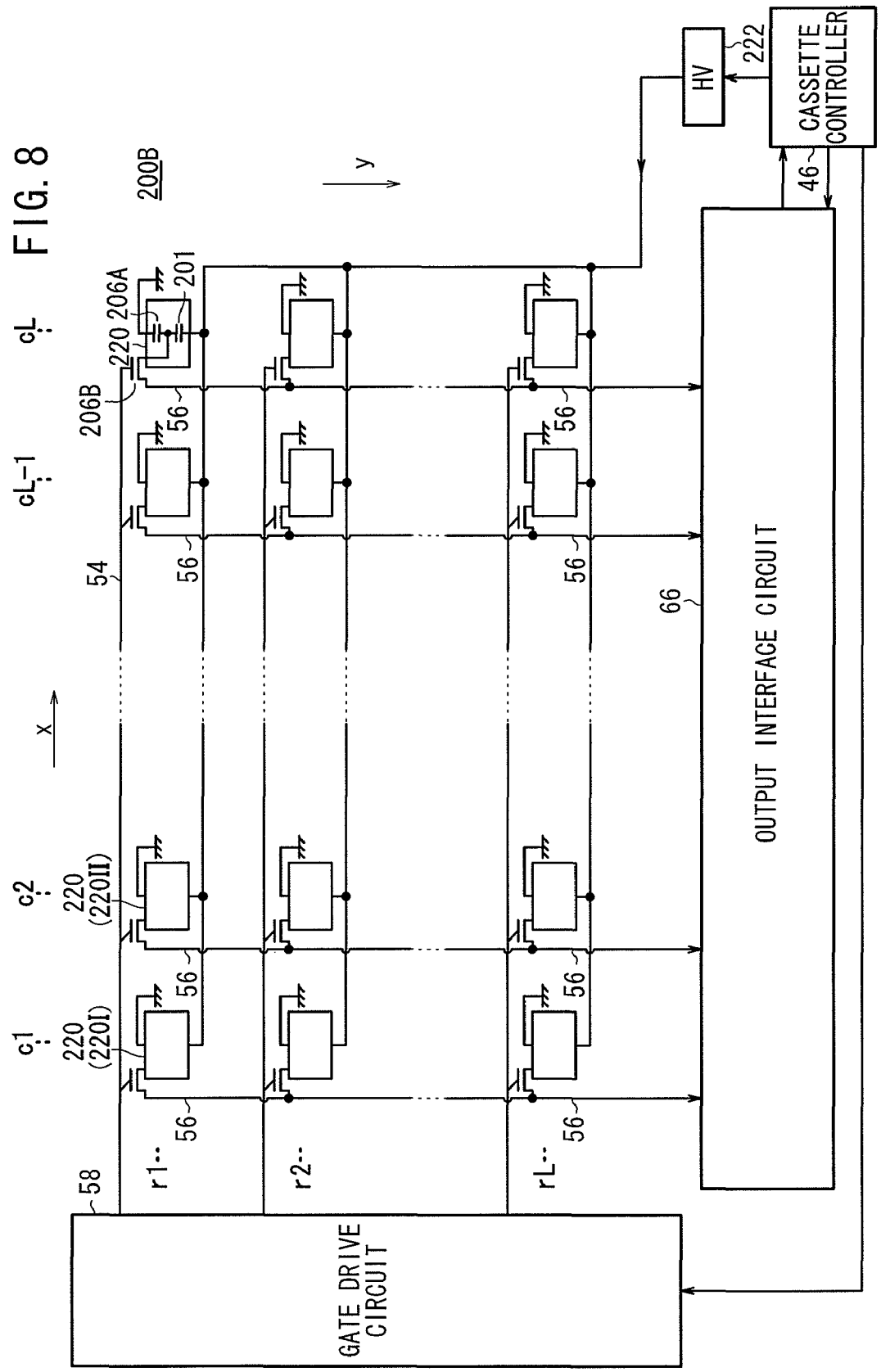
FIG. 8 is a block diagram of a circuit arrangement of a radiation detector according to another embodiment of the present invention.
Figure 9:
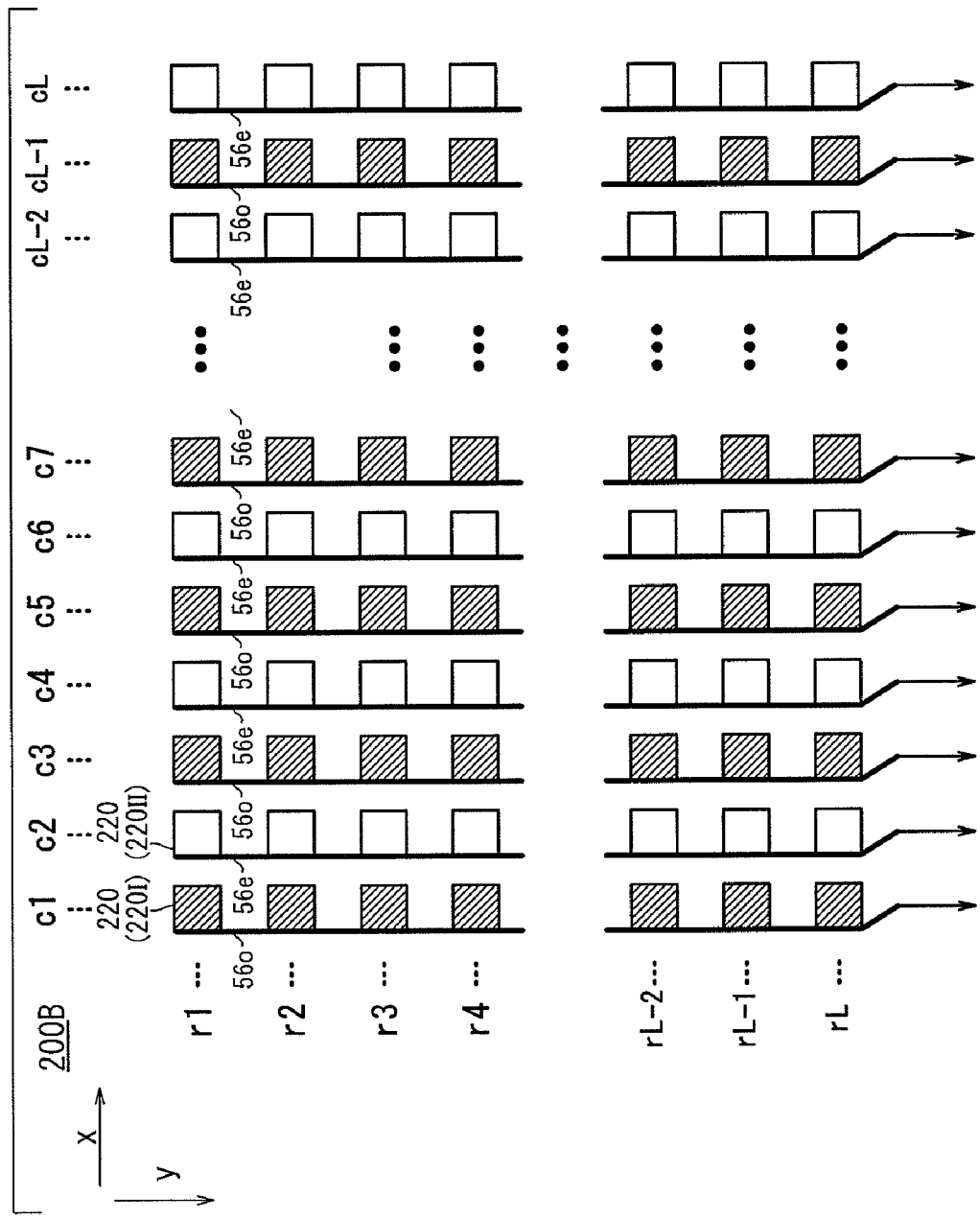
FIG. 9 is a diagram illustrative of the manner in which the radiation detector shown in FIG. 8 operates.

FIGS. 8 and 9 show a radiation detector (radiation conversion panel) 200B according to another embodiment of the present invention. In the radiation detector 200B, instead of the checkered pattern, two adjacent signal lines 56 are arranged in parallel to each other, not crossing each other. The radiation detector 200B comprises a first pixel group 220I connected to signal lines 56*o* in odd number columns and a second pixel group 220II connected to signal lines 56*e* in even number columns. That is, pixels 220 in odd number columns make up the first pixel group 220I, while pixels 220 in even number columns make up the second pixel group 220II.

In the radiation image capturing systems according to the embodiments, the radiation detector 200 housed in the cassette 24 directly converts the dose of the applied radiation X into an electric signal with the photoelectric conversion layer 201. However, the radiation image capturing systems may employ a radiation detector including a scintillator for converting the applied radiation X into visible light and a solid-state detecting device such as of amorphous silicon (a-Si) or the like for converting the visible light into an electric signal (see Japanese Patent No. 3494683).

Incidentally, instead of a TFT device, such a device as a CCD (Charge Coupled Device), a CMOS (Complementary Metal Oxide Semiconductor) device or the like may be used for a radiation detector.

Although certain preferred embodiments of the present invention have been shown and described in detail, it should be understood that various changes and modifications may be made therein without departing from the scope of the appended claims.

What is claimed is:

1. A method of capturing a radiation image according to dual-energy radiography, using a radiation conversion panel having a matrix of pixels for generating electric charges depending on a radiation that has passed through a subject, said radiation conversion panel comprising a first pixel group and a second pixel group, wherein pixels of said first pixel group and pixels of said second pixel group are arranged alternately, said method comprising:

a step A of performing a high energy-level image capturing cycle and thereafter reading electric charges from the pixels of said first pixel group to generate high energy-level first-pixel-group data;

a step B of performing a low energy-level image capturing cycle and reading electric charges from the pixels of said second pixel group to generate high energy-level second-pixel-group data, said electric charges from the pixels of said second pixel group comprising combined electric charges of the electric charges stored due to the low energy-level image capturing cycle and the electric charges remaining after the high energy-level image capturing cycle in said step A, in the pixels of said second pixel group;

a step C of reading electric charges from the pixels of said first pixel group, to generate low energy-level first-pixel-group data;

a step D of copying said low energy-level first-pixel-group data generated in said step C, as low energy-level second-pixel-group data of said second pixel group; and a step E of generating subtractive image data based on high energy-level all-pixel data and low energy-level all-pixel data, said high energy-level all-pixel data comprising said high energy-level first- and second-pixel-group data, and said low energy-level all-pixel data comprising said low energy-level first- and second-pixel-group data.

2. A method according to claim 1, wherein the pixels of said first pixel group and the pixels of said second pixel group are arranged in a checkered pattern.

3. A method of capturing a radiation image according to dual-energy radiography, using a radiation conversion panel having a matrix of pixels for generating electric charges depending on a radiation that has passed through a subject, said radiation conversion panel comprising a first pixel group and a second pixel group, wherein pixels of said first pixel group and pixels of said second pixel group are arranged alternately, said method comprising:

a step a of performing a low energy-level image capturing cycle and thereafter reading electric charges from the pixels of said first pixel group to generate low energy-level first-pixel-group data;

a step b of performing a high energy-level image capturing cycle and reading electric charges from the pixels of said first and second pixel groups to generate high energy-level all-pixel data;

a step c of copying said low energy-level first-pixel-group data generated in said step a, as low energy-level second-pixel-group data of said second pixel group; and a step d of generating subtractive image data based on said high energy-level all-pixel data and low energy-level all-pixel data, said low energy-level all-pixel data comprising said low energy-level first- and second-pixel-group data.

4. A method according to claim 3, wherein the pixels of said first pixel group and the pixels of said second pixel group are arranged in a checkered pattern.

\* \* \* \* \*